United States Patent [19]
Hale

[11] Patent Number: 5,089,384
[45] Date of Patent: Feb. 18, 1992

[54] METHOD AND APPARATUS FOR SELECTIVE CELL DESTRUCTION USING AMPLIFIED IMMUNOFLUORESCENCE

[75] Inventor: Michael O. Hale, Bellevue, Wash.

[73] Assignee: AMOCO Corporation, Chicago, Ill.

[21] Appl. No.: 267,264

[22] Filed: Nov. 4, 1988

[51] Int. Cl.⁵ .................. C12N 13/00; C12M 1/42
[52] U.S. Cl. ........................ 435/2; 435/173; 435/291; 435/311; 422/22; 250/461.2; 356/36; 356/318; 604/4
[58] Field of Search .............. 435/261, 311, 7, 288, 435/291, 173, 287, 2, 7.21, 7.23; 424/3, 7.1; 436/519; 356/36, 317, 318; 250/461.2; 372/9, 92, 94; 422/21-25.1; 604/4-6

[56] References Cited

U.S. PATENT DOCUMENTS

| | | | |
|---|---|---|---|
| 3,031,077 | 4/1962 | Mumma et al. | 209/111.5 |
| 3,305,089 | 8/1965 | Fraenkel. | |
| 3,684,377 | 8/1972 | Adams et al. | 356/36 |
| 3,710,933 | 1/1973 | Fulwyler et al. | 209/111.7 |
| 3,826,364 | 7/1974 | Bonner et al. | 209/111.5 |
| 3,871,770 | 3/1975 | von Behrens et al. | 356/39 |
| 3,883,247 | 5/1975 | Adams | 356/39 |
| 3,918,812 | 11/1975 | Holm | 356/73 |
| 4,156,570 | 5/1979 | Wardlaw | 356/36 |
| 4,186,838 | 2/1980 | Levitt et al. | 209/581 |
| 4,284,412 | 8/1981 | Hansen et al. | 356/39 |
| 4,321,133 | 3/1982 | DiGiacomo | 209/576 |
| 4,323,159 | 4/1982 | Wolf | 209/576 |
| 4,334,016 | 6/1982 | Furukawa | 435/7 |
| 4,360,539 | 11/1982 | Sachtleben et al. | 209/576 |
| 4,368,047 | 1/1983 | Andrade et al. | 435/7 |
| 4,395,397 | 7/1983 | Shapiro | 435/7 |
| 4,421,860 | 12/1983 | Elings et al. | 436/518 |
| 4,423,814 | 1/1984 | White | 209/3.3 |
| 4,532,723 | 8/1985 | Kellie et al. | 356/73 |
| 4,550,017 | 10/1985 | Liu et al. | 424/11 |
| 4,599,304 | 7/1986 | Lanier et al. | 435/7 |
| 4,599,307 | 7/1986 | Saunders et al. | 435/34 |
| 4,607,007 | 8/1986 | Lanier et al. | 435/7 |
| 4,615,878 | 10/1986 | Kass | 424/3 |
| 4,620,908 | 11/1986 | VanDuzer | 204/157.68 |
| 4,654,312 | 3/1987 | Chang et al. | 436/519 |
| 4,663,522 | 5/1987 | Welbourn et al. | 250/223 |
| 4,680,275 | 7/1987 | Wagner et al. | 436/518 |
| 4,723,659 | 2/1988 | Billion | 209/576 |
| 4,741,999 | 5/1988 | Genco et al. | 435/7 |
| 4,751,179 | 6/1988 | Ledis et al. | 435/34 |
| 4,772,552 | 9/1988 | Hercend et al. | 435/7 |

OTHER PUBLICATIONS

Gower, "Phase Conjugate Mirrors Tutorial T8", The International Society for Optical Engineering (1984).

*Primary Examiner*—David L. Lacey
*Assistant Examiner*—William H. Beisner
*Attorney, Agent, or Firm*—Seed and Berry

[57] ABSTRACT

A method and apparatus for altering pathogenic microorganisms and viruses in a bodily fluid. The microorganisms or viruses to be altered are tagged by immunofluorescent antibodies and placed in an illumination area where each of them fluoresces. A portion of the fluorescent radiation is received by an optical amplifier which amplifies the fluorescent radiation and redirects the fluorescent radiation back onto the cell from which it originated. The resonant cavity of the optical amplifier can be either a linear cavity or a ring cavity.

25 Claims, 1 Drawing Sheet

METHOD AND APPARATUS FOR SELECTIVE CELL DESTRUCTION USING AMPLIFIED IMMUNOFLUORESCENCE

TECHNICAL FIELD

This invention relates to a method and apparatus for selectively destroying cells, and more particularly, to a method and apparatus for amplifying fluorescent light from a tagged cell and refocussing the amplified light back onto the original cell.

BACKGROUND ART

Physicians and other medical practitioners are keenly interested in methods and apparatus for treating pathogenic microorganisms and viruses contained in a living human body. In addition, they are interested in treating host cells that undergo transformation into cancer cells.

A wide variety of treatments for tumors, including chemotherapy and photodynamic therapy (PDT), have been developed for this purpose. Chemotherapy treats tumors through chemicals which have been injected into the body to attack a particular type of cell. PDT treats a tumor by coating its surface with a dye, such as hemato porphyrine derivative (HPD), which responds to light by creating singlet oxygen species. These species destroy the tumor membrane structures.

Such chemically based treatments are necessarily limited to the use of chemicals which are generally toxic to only one type of cell. These techniques rely on the chemical being more toxic to the unwanted cell than to the body. This imposes severe restrictions on the chemicals which can be used.

Treatments for less massive undesirable cellular materials, such as viruses contained in bodily fluids, are also generally chemically based, since this is a very effective way to get the treatment to each of the targeted cells. For example, PDT can also be used to treat undesirable cellular material in blood.

Unfortunately, PDT has serious disadvantages. For example, those who are undergoing PDT must avoid exposure to sunlight for approximately two days after undergoing the treatment. In addition, chemotherapy and PDT also affect nontargeted cells.

As disclosed in U.S. Pat. No. 4,395,397, Shapiro has investigated using fluorescence from tagged cells to trigger a pulsed laser which killed the fluorescing cells. However, to the applicant's knowledge, no one has investigated using imaging techniques to amplify and re-direct the fluorescing light back onto the cell for treatment. This technique has the advantages of both chemical and physical techniques: many cells can be accessed simultaneously with chemical tagging, while cell destruction takes place only from the amplified and refocussed light.

It is therefore desirable to relax the chemical restrictions imposed by chemotherapy and photodynamic therapy by using selective tagging of the undesirable cells, followed by a non-chemical technique for tagged cell destruction.

DISCLOSURE OF THE INVENTION

It is an object of the present invention to relax the restrictions on chemicals which can be used to treat pathogenic microorganisms and viruses.

It is another object of the present invention to relax the restrictions on chemicals which can be used to treat host cells that undergo transformation into cancer cells.

It is yet another object of the present invention to provide an optical technique that can be used to alter pathogenic cells, thereby rendering them harmless.

It is a further object of the present invention to provide a technique which can efficiently treat a large number of pathogenic cells in a relatively short period of time.

According to one aspect, the invention provides an apparatus for altering a cell belonging to a predesignated class of cells in a bodily fluid. The apparatus includes means for tagging the cell with a chemical group that fluoresces. In this way, the tagged cell produces fluorescent electromagnetic radiation at a first wavelength when illuminated by electromagnetic energy at a second wavelength. The apparatus also includes means for illuminating the tagged cell with electromagnetic energy containing the second wavelength. Further, the apparatus includes means for receiving a portion of the fluorescent radiation at the first wavelength produced by the tagged cell. Also, the apparatus includes means for amplifying the received fluorescent radiation and means for directing the amplified fluorescent radiation onto the tagged cell with sufficient intensity to alter the cell.

In another aspect, the invention provides a method for altering a cell belonging to a predesignated class of cells in a bodily fluid. The method comprises the steps of (A) tagging the cell with a chemical group that fluoresces to produce fluorescent electromagnetic radiation at a first wavelength when illuminated by electromagnetic energy at a second wavelength, (B) illuminating the tagged cell with electromagnetic energy containing a second wavelength, (C) receiving a portion of the fluorescent radiation at the first wavelength produced by the tagged cell, (D) amplifying the received fluorescent radiation, and (E) directing the amplified fluorescent radiation onto the tagged cell with sufficient intensity to alter the cell.

BEST MODES FOR CARRYING OUT THE INVENTION

Figure 1:
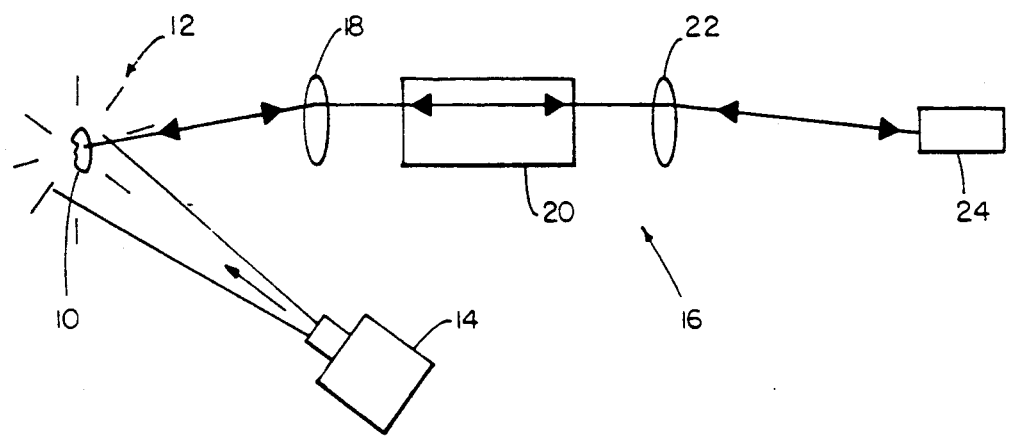
FIG. 1 is a schematic diagram of a first embodiment of the invention.

The present invention provides a physical aid to an immune system against pathogenic microorganisms and viruses, and possibly host cells that undergo transformation into cancer cells. The invention uses optical instruments to irreparably destroy, damage, or alter a tagged cell for the immune system.

Researchers have investigated optical cell damage and tissue damage as related to laser body surgery, laser angioplasty and laser eye surgery. This treatment differs from known chemical techniques, since it relies on both physical and chemical techniques.

Briefly, the cells to be treated are tagged with fluorescent monoclonal antibodies. They are then illuminated with an ultraviolet light source which causes the fluorescent part of the monoclonal antibody attached to the cell to fluoresce, providing a cell marker for tracking and targeting. The fluorescence from some small volume of the sample is collected and sent through a high gain medium to amplify the fluorescent radiation. The amplified light is focused back onto the tagged cells. If the amplification of the device is sufficiently high, the returning light will alter the tagged cells. The cell alteration can either be direct (e.g., to the cell walls) or indirect disruption of cellular processes via light absorption and subsequent cell heating. Alternatively, the induced changes in the cell structure may cause the immune system to attack the altered cell.

The human blood stream contains approximately 5 million red blood cells and 8 thousand white blood cells per microliter. In an adult human, whose total blood volume is approximately 5 liters, there are an approximate total of $4 \times 10^{10}$ white blood cells (and approximately one thousand times as many red blood cells). In the event of an infection, the population of invading cells can be approximately as large as this order of magnitude. If a clinical device purifies an individual's blood in an hour (by removing the invading cells), it must be capable of destroying approximately 11.1 million cells per second.

Digital logic techniques to distinguish between good and bad cells cannot approach these rates ($10^7$ per second). Neither can a single event analog logic technique that might trigger an external laser. Only an analog logic technique that can distinguish, target, and destroy many cells simultaneously will work in this application.

An average red blood cell is approximately 10 micrometers in diameter and one micrometer thick. Since the cells are packed in a fluid, the average distance between any two adjacent cells is on the order of a few micrometers. Accordingly, any treatment of such cells must be very tightly focused and accurately pointed in order to destroy a given cell without destroying its neighbors. An appropriate choice to apply this treatment is an optical amplifier.

The analog logic technique discussed above is needed to distinguish between good and bad cells. Currently, the technique used by the medical community to tag cells or chemically treat cells with the highest specificity is to use monoclonal antibodies. These are clones of stable antibodies that will attach to a particular type of cell with high specificity. The monoclonal antibody can contain fluorescing chemical groups which, when they attach to their target cells, cause the cells to fluoresce. Two particular types of immunofluorescence are provided by fluorescein isothiocyanate and rhodamine B isothiocyanate. These and other fluorescing groups attached to antibodies provide sufficient light at a first wavelength under illumination by light at a second wavelength to isolate many types of cells.

Referring to FIG. 1, a first embodiment of an apparatus according to the present invention includes a linear optical amplifier system. The fluid containing fluorescently tagged cells 10 passes through an illumination area, indicated generally by reference numeral 12. The illumination area 12 is illuminated by an illuminator 14 which produces electromagnetic energy, such as light energy, containing the second wavelength. As a result of this illumination by the illuminator 14, the fluorescently tagged cells 10 radiate fluorescent electromagnetic energy, such as light energy, at the first wavelength. A portion of the fluorescent radiation is received by a linear optical amplifier system, generally indicated by reference number 16. The linear optical amplifier system 16 includes an optical element 18, such as a focusing lens, which directs the fluorescent radiation to a gain medium 20, such as a titanium-doped sapphire crystal, organic dyes, or optically pumped atomic transition gas which provide high amplification in a small volume. The gain medium 20 is capable of amplifying electromagnetic energy passing through it in either of two directions. Therefore, the fluorescent radiation directed by the optical element 18 is amplified as it makes a first pass through the gain medium 20.

The amplified radiation is directed, by means of another optical element 22, such as a lens, onto a reflective optical element 24. The optical element 24 can take the form of a phase conjugate mirror. The amplified radiation is then reflected back through the optical element 22 to the gain medium 20, where it is further amplified on its second pass. The highly amplified radiation is next directed through optical element 18 onto the illumination area 12. In particular, the optical amplifier system 16 is adjusted, through proper choice and orientation of the optical elements 18, 22 and 24, to cause the amplified fluorescent radiation produced by a particular tagged cell to be redirected back onto that cell with sufficient power to alter or even destroy the cell. If the optical element 24 is chosen to be a phase conjugate mirror, it will focus the fluorescent radiation back onto the particular cell no matter where that cell is located in the illumination area 12.

Figure 2:
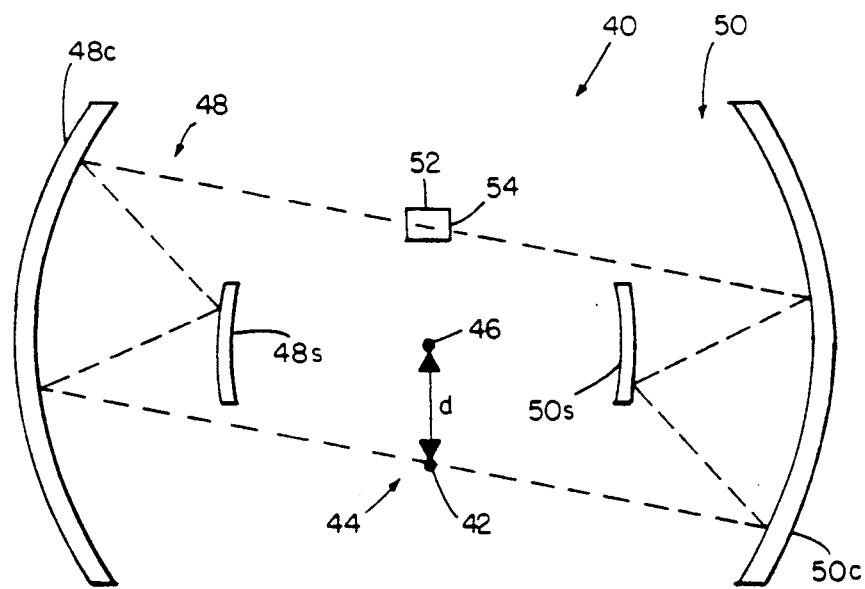
FIG. 2 is a schematic diagram of a second embodiment of the invention.

FIG. 2 is a schematic diagram of a second embodiment of the invention, involving a ring optical amplifier. The apparatus 40 includes conventional means for causing fluorescently tagged cells 42 to pass through an illumination area 44 which is displaced from a point 46 by a distance d. The illumination area 44 is illuminated by electromagnetic energy containing the second wavelength (illuminator not shown).

The apparatus 40 also includes two concentric mirror pairs 48 and 50. Both mirrors in each pair are concentric with respect to a point 46. Each mirror pair 48 and 50 includes a small mirror (48S and 50S) and a large mirror (48L and 50L). The concave sides of the large mirrors 48L and 50L and the convex sides of the small mirrors 48S and 50S are coated with a layer (such as silvering) that reflects any of the fluorescent radiation that strikes them. Accordingly, a portion of the fluorescent radiation that is produced by the fluorescing cell 42 in the illumination area 44 is captured by the concave surface of the large mirror 48L, reflected onto the convex surface of the small mirror 48S, and rereflected onto the concave surface of the large mirror 48L. When this reflected fluorescent radiation is further reflected by the large mirror 48L, it is directed along a path that is parallel to the path it followed when it was first received by the large mirror 48L.

Regardless of its direction of departure from the illumination area 44, the fluorescent radiation captured by the large mirror 48L is reflected to a point 52 which is colinear with the location of the cell 42 and the point 46 and separated from the point 46 by a distance equal to the distance between the cell 42 and the point 46. In other words, the point 46 is located at the mid point of the straight line extending between the cell 42 and the point 52. A gain medium 54 is located to include the point 52 and, accordingly, receives all of the fluorescent radiation received by the large mirror 48L.

The gain medium 54 amplifies the fluorescent radiation received by the large mirror 48L and directs it toward the large mirror 50L. By a process analogous to that just described, the amplified fluorescent radiation is reflected from the concentric mirrors 50L and 50S and then redirected toward the fluorescing cell 42. By proper arrangement of the optical elements comprising the mirror pairs 48 and 50 and the gain medium 54, the amplified fluorescent radiation is focused on the particular cell 42 which first generated that component of fluorescent radiation. By this method, the tagged fluorescing cells create the electromagnetic light energy which is then amplified and used to alter the originating cells.

While the foregoing descriptions are directed toward two preferred embodiments of the invention, one skilled in the art will readily appreciate that various modifications of the above-described embodiments may be made without departing from the spirit and the scope of the invention. Accordingly, the spirit and the scope of the present invention are to be limited only by the following claims.

I claim:

1. Apparatus for altering a cell belonging to a predesignated cell class in a bodily fluid, comprising:
   a source of fluorescing and tagging chemical group for tagging the cell, wherein said chemical group fluoresces to produce fluorescent electromagnetic energy at a first wavelength when illuminated by electromagnetic energy at a second wavelength;
   means for illuminating the tagged cell with illuminating electromagnetic energy at said second wavelength;
   means for receiving a portion of said fluorescent electromagnetic energy at said first wavelengthh produced by the tagged cell;
   means for amplifying said received fluorescent electromagnetic energy at said first wavelength; and
   means for directing said amplified fluorescent electromagnetic energy at said first wavelength back onto the tagged cell with sufficient intensity to alter the cell.

2. The apparatus of claim 1, wherein said chemical group emits light energy and said means for illuminating illuminates light energy.

3. The apparatus of claim 1 wherein said chemical group comprises an antibody.

4. The apparatus of claim 1 wherein said chemical group comprises a monoclonal antibody.

5. The apparatus of claim 1 wherein said amplifying means comprises a gain medium constructed so as to amplify said received portion of said fluorescent electromagnetic energy at said first wavelength.

6. Apparatus for altering a cell belonging to a predesignated cell class in a bodily fluid, comprising:
   a source of fluorescing and tagging chemical group for tagging the cell, wherein said chemical group fluoresces to produce fluorescent electromagnetic radiation at a first wavelength when illuminated by electromagnetic energy at a second wavelength;
   means for illuminating the tagged cell with illuminating electromagnetic energy at said second wavelength; and
   an optical cavity constructed and arranged so as to receive, amplify, and direct a portion of said fluorescent electromagnetic energy at said first wavelength back onto the tagged cell with sufficient intensity to alter the cell.

7. The apparatus of claim 6 wherein said optical cavity comprises:
   a receiving optical element constructed and arranged so as to receive said portion of said fluorescent electromagnetic energy at said first wavelength;
   optical means for amplifying said received portion of said fluorescent electromagnetic energy at said first wavelength; and
   a directing optical element constructed and arranged so as to direct said amplified fluorescent electromagnetic energy at said first wavelength onto the tagged cell.

8. The apparatus of claim 7 wherein said optical means comprises a gain medium.

9. The apparatus of claim 8 wherein said gain medium is constructed so as to amplify said fluorescent electromagnetic energy at said first wavelength in two consecutive passes through said gain medium, said consecutive passes being in opposite directions.

10. The apparatus of claim 9 wherein said optical means further comprises a reflecting optical element constructed and arranged so as to reflect said fluorescent electromagnetic energy at said first wavelength toward said gain medium after a first of said two consecutive passes.

11. The apparatus of claim 10 wherein said reflecting optical element is a phase conjugate mirror.

12. The apparatus of claim 8 wherein said receiving optical element is constructed so as to direct said fluorescent electromagnetic energy at said first wavelength onto said gain medium and said directing optical element is constructed so as to receive said amplified fluorescent electromagnetic energy at said first wavelength.

13. The apparatus of claim 12 wherein said receiving optical element and said directing optical element are separate pairs of concentric mirrors.

14. Apparatus for altering a cell belonging to a predesignated cell class in a bodily fluid, comprising:
   a source of fluorescing and tagging chemical group for tagging the cell, wherein said chemical group fluoresces to produce fluorescent light at a first wavelength when illuminated by light at a second wavelength;
   means for causing the tagged cell to pass through an illuminatin area;
   means for illuminating said illumination area with illuminating light at said second wavelenth, thereby causing the tagged cell to fluoresce when it is in said illumination area;
   a linear resonant optical cavity constructed and arranged so as to amplify a portion of said fluorescent light; and
   means for directing said amplified fluorescent light onto the cell with sufficient intensity to alter the cell.

15. The apparatus of claim 14 wherein said linear resonant optical cavity comprises a phase conjugate mirror.

16. The apparatus of claim 14 wherein said chemical group is a fluorescent monoclonal antibody.

17. Apparatus for altering a cell belonging to a predesignated cell class in a bodily fluid, comprising:
   a source of fluorescing and tagging chemical group for tagging the cell, wherein said chemical group fluoresces to produce fluorescent light at a first wavelength when illuminated by light at a second wavelength;
   means for causing the tagged cell to pass through an illumination area;
   means for illuminating said illumination area with illuminating light at said second wavelength, thereby causing the tagged cell to fluoresce while in said illumination area;

a ring resonant optical cavity constructed and arranged so as to amplify a portion of said fluorescent light; and means for directing said amplified fluorescent light onto the cell with sufficient intensity to alter the cell.

18. The apparatus of claim 17 wherein said ring resonant optical cavity comprises a gain medium.

19. The apparatus of claim 18 wherein said ring resonant optical cavity further comprises first and second pairs of concentric mirrors, said concentric mirrors having a common center located approximately at the mid point of the straight line between the illumination area and the gain medium.

20. The apparatus of claim 19 wherein each of said pairs of concentric mirrors comprises a larger radius mirror and a smaller radius mirror, said larger radius mirror being reflective on its concave surface and said smaller radius mirror being reflective on its convex surface.

21. The apparatus of claim 18 wherein said gain medium is made from titanium-doped sapphire.

22. The apparatus of claim 18 wherein said gain medium is made from organic laser dye.

23. The apparatus of claim 18 wherein said gain medium is made from an optically pumped atomic gas.

24. A method for altering a cell belonging to a predesignated cell class in a bodily fluid, comprising the steps of:

(A) tagging said cell with a chemical group that fluoresces to produce fluorescent electromagnetic energy at a first wavelength when illuminated by electromagnetic energy at a second wavelength;

(B) illuminating said tagged cell with illuminating electromagnetic energy at said second wavelength;

(C) receiving a portion of said fluorescent electromagnetic energy at said first wavelength produced by said tagged cell;

(D) amplifying said received fluorescent electromagnetic energy at said first wavelength; and (E) directing said amplified fluorescent electromagnetic energy at said first wavelength onto said cell with sufficient intensity to alter said cell.

25. A method for altering a cell belonging to a predesignated cell class in a bodily fluid, comprising the steps of:

(A) tagging said cell with a chemical group that fluoresces to produce fluorescent light at a first wavelength when illuminated by light at a second wavelength;

(B) causing said tagged cell to pass through an illumination area;

(C) illuminating said illumination area with light containing said second wavelength, thereby causing said tagged cell to fluoresce while in said illumination area;

(D) amplifying a portion of said fluorescent light in a linear resonant optical cavity; and (E) directing said amplified fluorescent light onto said cell with sufficient intensity to alter said cell.

* * * * *